(12) United States Patent
Crawford et al.

(10) Patent No.: US 7,723,525 B2
(45) Date of Patent: May 25, 2010

(54) CHEMOKINE-BINDING HETEROCYCLIC COMPOUND SALTS, AND METHODS OF USE THEREOF

(75) Inventors: Jason B. Crawford, Burnaby (CA); Yongbao Zhu, Coquitlam (CA); Gang Chen, Langley (CA); Ian R. Baird, Abbotsford (CA); Renato T. Skerlj, Vancouver (CA)

(73) Assignee: Genzyme Corporation, Cambridge, MA (US)

( * ) Notice: Subject to any disclaimer, the term of this patent is extended or adjusted under 35 U.S.C. 154(b) by 735 days.

(21) Appl. No.: 11/235,469

(22) Filed: Sep. 26, 2005

(65) Prior Publication Data

US 2006/0069122 A1 Mar. 30, 2006

Related U.S. Application Data

(60) Provisional application No. 60/614,790, filed on Sep. 29, 2004.

(51) Int. Cl.
*C07D 215/38* (2006.01)
(52) U.S. Cl. .................................. 546/157; 546/163
(58) Field of Classification Search ................ 546/157, 546/163; 514/312
See application file for complete search history.

(56) References Cited

U.S. PATENT DOCUMENTS

| 5,583,131 A | 12/1996 | Bridger | |
|---|---|---|---|
| 5,698,546 A | 12/1997 | Bridger | |
| 5,817,807 A | 10/1998 | Bridger | |
| 7,332,605 B2* | 2/2008 | Crawford et al. | 546/171 |
| 7,354,932 B2* | 4/2008 | Bridger et al. | 514/313 |
| 7,354,934 B2* | 4/2008 | Bridger et al. | 514/314 |
| 2003/0232808 A1* | 12/2003 | Kobayashi et al. | 514/218 |
| 2003/0232863 A1* | 12/2003 | Bayly et al. | 514/357 |
| 2003/0232889 A1* | 12/2003 | Barrett et al. | 514/619 |
| 2003/0236262 A1* | 12/2003 | Bakshi et al. | 514/249 |

FOREIGN PATENT DOCUMENTS

| WO | 03/055876 | * | 7/2003 |
|---|---|---|---|
| WO | WO-03/055876 | | 7/2003 |
| WO | WO-2004/106493 | | 12/2004 |

OTHER PUBLICATIONS

International Search Report for PCT/US05/34491, mailed on Apr. 11, 2006, 2 pages.
Database CA on STN, Chemical Abstracts, No. 139:101128.
Carroll et al., Science (1997) 276:274-276.
Lukacs et al., Am. J. Pathology (2002) 160(4):1353-1360.
Matthys et al., J. Immunol. (2001) 167:4686-4692.
Ponath, Exp. Opin. Invest. Drugs (1998) 7:1-18.

* cited by examiner

*Primary Examiner*—D. Margaret Seaman
(74) *Attorney, Agent, or Firm*—Morrison & Foerster LLP

(57) ABSTRACT

The present invention relates to chemokine-binding heterocyclic compound salts, methods of use thereof, and methods for preparing the same.

10 Claims, No Drawings

CHEMOKINE-BINDING HETEROCYCLIC COMPOUND SALTS, AND METHODS OF USE THEREOF

CROSS REFERENCE TO RELATED APPLICATIONS

This application claims the benefit of U.S. provisional patent application Ser. No. 60/614,790, filed Sep. 29, 2004, the contents of which are incorporated herein by reference in their entirety.

TECHNICAL FIELD

The present invention relates to chemokine-binding heterocyclic compound salts, methods of use thereof, and methods for preparing the same.

BACKGROUND OF THE INVENTION

The chemotactic cytokines, or chemokines, are a family of proteins, approximately 8-10 kDa in size that function, at least in part by modulating a complex and overlapping set of biological activities important for the movement of lymphoid cells and extravasation and tissue infiltration of leukocytes in response to inciting agents (see, for example: P. Ponath, *Exp. Opin. Invest. Drugs*, 7:1-18, 1998). The cellular receptors for these proteins are classified based on the chemokine natural ligand. Receptors of the β-chemokines are designated with the prefix "CCR" whereas the receptors of the α-chemokine are designated with the prefix "CXCR". The natural chemokine ligand for the CXCR4 receptor is stromal cell-derived factor-1 (SDF-1).

The inhibition of the binding of SDF-1 to CXCR4 by specific small-molecule inhibitors has been shown, in a model, to reduce the severity of the pathogenesis of collagen II-induced arthritis (P. Matthys, S. Hatse, K. Vermiere, A. Wuyts, G. Bridger, G. W. Henson, E. De Clercq, A. Billiau and D. Schols, *J. Immunol.* 107: 4686-4692, 2001). This model, which is used as a study model for the pathogenesis of rheumatoid arthritis in humans, shows that SDF-1 plays a central role in the pathogenesis of murine collagen induced arthritis. Similarly, the use of small-molecule CXCR4 inhibitors has been shown, in a murine model, to reduce a number of pathological parameters related to asthmatic-type inflammation in an allergin-induced inflammation (N. W. Lukacs, A. Berlin, D. Schols, R. T. Skerlj, G. J. Bridger, *Am. J. Pathology*, 160 (4): 1353-1360, 2002).

Two specific chemokine receptors, CXCR4 and CCR5, have been implicated in the etiology of infection by human immunodeficiency virus (HIV). The T cell-line tropic (T-tropic) viral phenotype of HIV requires, for infection, an association with the CXCR4 receptor, which is expressed in the surface of certain cells of the immune system (Carroll et al., *Science*, 276: 274-276, 1997). Specifically, an interaction between HIV and the CXCR4 receptor is required for membrane fusion, a necessary step in the infection of the host immune cell.

The heterocyclic compounds disclosed in U.S. Pat. No. 5,583,131, U.S. Pat. No. 5,698,546 and U.S. Pat. No. 5,817,807 selectively bind to the CXCR4 receptor, inhibiting the binding of the natural SDF-1 ligand. Such binding may show anti-inflammatory effects. The binding also competitively prevents the binding of the T-tropic HIV with the receptor, and thus imparts a preventative effect against HIV infection.

The compound of Formula I, (S)-(N'-(1H-benzimidazol-2-ylmethyl)-N'-5,6,7,8-tetrahydroquinolin-8-yl-1,4-butanediamine, is disclosed and claimed along with salts, pro-drug forms, and stereoisomeric forms thereof in WO 03055876, the entire disclosure of which is incorporated herein by reference. Preferably among the pharmaceutically acceptable salts described in WO 03055876 and the only salt form prepared therein is the hydrobromide salt. The compound of the Formula I is intended to be used as an orally dosed pharmaceutical agent in the treatment of HIV infections, and the present salts of Formula I suffer from problems associated with hygroscopicity.

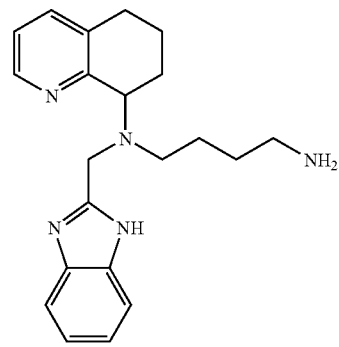

I

Citation of the above documents is not intended as an admission that any of the foregoing is pertinent prior art. All statements as to the date or representation as to the contents of these documents is based on the information available to the applicants and does not constitute any admission as to the correctness of the dates or contents of these documents. Further, all documents referred to throughout this application are incorporated in their entirety by reference herein.

SUMMARY OF THE INVENTION

The present invention provides new pharmaceutically acceptable salts of Formula I, and methods for preparing the same. The present invention also provides methods for using the pharmaceutically acceptable salts of the present invention.

In one aspect, the present invention provides a method for preparing a crystalline salt of the Formula I, using an organic acid as a counter ion. In a particular example, the present invention provides a method for preparing a salt of Formula I, comprising contacting a compound of Formula I with an acid in a solvent to obtain a salt of a compound of Formula I, wherein said salt is citrate, edetate, lactate, maleate, mandelate, mesylate, terephthalate, substituted or unsubstituted benzoate, orotate, substituted benzenesulfonate, naphthoate, napsylate, or tosylate.

In a particular example, the acid is a benzoic acid, optionally substituted with an organic or inorganic substituent known in the art. For example, the acid may be a benzoic acid substituted with hydroxy or amino.

In the above method, the ratio of the organic acid to the compound of Formula I may be about 1:1. Alternatively, the ratio of the organic acid to the compound of Formula I may be about 2:1 or 3:1.

In the above method, the solvent may comprise an alcohol, and may further comprise an aqueous medium. In one embodiment, a solution of the compound of Formula I and the acid is concentrated until the resulting solution becomes cloudy compared to the solution prior to concentration. Furthermore, a solution of the compound of Formula I and the acid may be seeded with a salt. In particular examples, the acid is 4-hydroxybenzoic acid in a solvent comprising alcohol and water. The alcohol may be heated prior to adding water, and water may be added until the resulting solution is cloudy compared to the solution prior to the addition of water. Examples of alcohol that may be used in the methods of the invention include but are not limited to methanol, ethanol, propanol, isopropanol, n-butanol, or a mixture thereof. In particular examples, the alcohol is methanol.

In particular examples, a compound of Formula I may be contacted with 4-hydroxybenzoic acid to provide a methanol solution having a molarity of about 0.5 M. The methanol solution may be heated to a temperature between 30 and 80 degrees Celsius, preferably to a temperature between 45 and 60 degrees Celsius, or more preferably, to about 50 degrees Celsius. In particular examples, approximately three volumes of water are added to the methanol solution, and the resulting solution is heated to about 50 degrees Celsius. The methanol solution may be seeded with a small amount of the crystalline 4-hydroxybenzoate salt of the compound of the Formula I. The methanol solution may also be cooled to precipitate a compound of Formula I as a crystalline 4-hydroxybenzoate salt.

The present invention provides methods for producing salts of Formula I that are more stable when stored in bulk prior to manufacturing, particularly prior to tableting. Furthermore, the current process avoids problems associated with hygroscopicity where absorption of moisture occurs upon storage. Because the drug may be effective in small dosages, dose accuracy is particularly important. The lessened tendency toward hygroscopicity is important because the accuracy of weighing out bulk compound for manufacturing and analytical purposes, particularly for tableting purposes, would be affected if the compound's weight is partially attributable to water of hydration. Thus, constant assaying would be required to ensure that the proper amount of active drug is provided.

The present invention also provides pharmaceutical salts that exhibit improved chemical and thermal stability than other salts. In particular examples, the present invention provides a pharmaceutically acceptable salt of a compound of the Formula I, wherein the salt is citrate, edetate, lactate, maleate, mandelate, mesylate, terephthalate, substituted or unsubstituted benzoate, orotate, substituted benzenesulfonate, naphthoate, napsylate, or tosylate. In particular examples, the salt is 4-hydroxybenzoate, 4-aminobenzoate, 4-hydroxybenzenesulfonate, 4-aminobenzenesulfonate, benzoate or orotate. In more particular examples, the salt is 4-hydroxybenzoate, 4-aminobenzoate, 4-hydroxybenzenesulfonate or 4-aminobenzenesulfonate. In yet more particular examples, the salt is 4-hydroxybenzoate. The present invention also provides pharmaceutical compositions comprising a salt of a compound of Formula I, and a pharmaceutically acceptable diluent.

Furthermore, the present invention provides a benzoate salt of a compound of Formula I, having less hydroscopicity than the hydrobromide or hydrochloric salt of said compound of Formula I. The benzoate salt is more stable in storage than the hydrobromide or hydrochloride salt of said compound of Formula I. The benzoate salt also has an improved stability as compared to the free base, when measured at about 30 degrees Celsius and above, or at about 40 degrees Celsius and above. In a particular example, the benzoate salt may be 4-hydroxybenzoate.

Further, the present invention provides methods for modulating a CXCR4 receptor, a CCR5 receptor, or both, comprising contacting a cell having the receptor with an effective amount of a pharmaceutical composition comprising a salt of a compound of Formula I as previously described, and a pharmaceutically acceptable diluent. In particular examples, the present invention provides a method for treating a condition mediated by a CXCR4 receptor, a CCR5 receptor, or both, comprising administering to a subject in need of such treatment an effective amount of the pharmaceutical salts and compositions of the present invention.

Examples of CXCR4 or CCR5 receptor mediated condition include but are not limited to angiogenesis, atherosclerosis or acute thrombosis, retroviral infections like HIV, arthritis such as rheumatoid arthritis, allergy, inflammatory disease such as neutrophil mediated acute respiratory distress syndrome and ischemia/reperfusion injury to chronic diseases such as asthma, or a tumor (solid or metastatic) including, but not limited to, glioblastoma, blood related cancer malignancies such as lymphoma (Hodgkin's and Non-Hodgkin's lymphoma), myeloma, fibroma, astrocytoma, acute and chronic leukemia and tumors of the Central Nervous System (CNS), i.e. epenymoglioma, medulloblastoma, oligodendoglioma and spongioblastoma. The tumor may be of brain, ovarian, breast, prostate, lung or haematopoetic tissue. Other examples of CXCR4 or CCR5 receptor mediated condition include allergic rhinitis, hypersensitivity lung diseases, hypersensitivity pneumonitis, eosinophilic pneumonias, delayed-type hypersensitivity, interstitial lung disease, systemic anaphylaxis or hypersensitivity responses, drug allergies, insect sting allergies, autoimmune diseases, psoriatic arthritis, systemic lupus erythematosus, myastenia gravis, juvenile onset diabetes, glomerulonephritis, autoimmune throiditis, graft rejection such as allograft rejection or graft versus host disease; inflammatory bowel diseases, Crohn's disease, ulcerative colitis, spondyloarthropathies, scleroderma, psoriasis, dermatitis, eczema, atopic dermatitis, allergic contact dermatitis, urticaria, vasculitis, eosinphilic myotis, eosiniphilic fasciitis, or a condition associated with immunosuppression.

In the above treatment methods, the subject may be human or animal. In particular examples, the subject may be undergoing chemotherapy, radiation therapy, wound healing, burn treatment, or therapy for autoimmune disease.

DETAILED DESCRIPTION OF THE INVENTION

The invention discloses methods of making novel salts of the compound of the Formula I. In general, the procedures involve the mixing of the basic compound of the Formula I with an acidic counter ion, followed by the isolation of the salt.

In one embodiment, the invention offers a simple process for the formation of a salt between the compound of the Formula I and a series of inorganic acids. The stoichiometric ratio of acid to Formula I can be varied. The following non-limiting list of suitable inorganic ions representing suitable acids for use in the formation of a salt with the compound of the Formula I includes, for example chloride, sulfate, phosphate, nitrate, bromide, fluoride, iodide.

In another embodiment, the present invention discloses a process for the formation of a salt between an organic acid and the compound of the Formula I. The following non-limiting list of organic ions representing suitable acids which may be used to form salts according to the procedures disclosed in the present invention includes, for example, acetate, aspartate, benzenesulfonate, citrate, edetate, lactate, maleate, mandelate, mesylate, D-tartrate, L-tartrate, terephthalate, 4-hydroxybenzoate, 4-aminobenzoate, orotate, 4-hydroxybenzenesulfonate, 4-aminobenzenesulfonate, benzoate, napthoate, napsylate, tosylate.

In another embodiment, the present invention discloses a novel process for the formation of a crystalline salt between an organic acid and the compound of the Formula I. Suitable organic anions include, for example, but are not limited to 4-hydroxybenzoate, 4-aminobenzoate, 4-aminobenzenesulfonate, 4-hydroxybenzenesulfonate, benzoate, benzenesulfonate, orotate.

The process is illustrated by the formation of a 4-hydroxybenzoate salt of the compound of the Formula I. In one example, a compound having Formula I is dissolved in a suitable solvent. A suitable solvent is typically an alcohol, which includes, but is not limited to methanol, ethanol, isopropanol, butanol or mixtures thereof. Non-limiting examples of other suitable solvents include dimethylformamide, N-methylpyrrolidine, ethylene glycol. Preferred solvents are methanol or ethanol or isopropanol. 4-hydroxybenzoic acid is then added as a solid or as a solution in the same solvent. The acid is typically used in a 1.0:1 to 1.2:1 molar ratio to the compound of the Formula I. The concentration of the compound of the Formula I in the chosen solvent is typically about 0.5 moles/L, or approximately 4.5 weight equivalents of solvent. The mixture is then stirred and heated to achieve solvation, which generally occurs at 30-80° C., and preferably at about 45-60° C. A second solvent is then added, which is typically water. Generally, about 8-10 weight equivalents are added, to achieve a slight cloudiness. The pH of the solution may optionally be adjusted at this point to a range between 7-8 with aqueous sodium hydroxide and/or hydrochloric acid. The mixture is then cooled, with stirring, to cause precipitation of the salt, usually as crystals. Seeding of the mixture during cooling may be performed. The salt is isolated by filtration.

The salts prepared by the described procedures exhibit desirable characteristics, when compared to the crystalline freebase, such as enhanced chemical and thermal stability.

Utility and Administration

The invention is directed to pharmaceutically acceptable salts and compositions of a compound of Formula I that modulate chemokine receptor activity. Chemokine receptors include but are not limited to CCR1, CCR2, CCR3, CCR4, CCR5, CXCR3, and CXCR4.

In one embodiment, the invention provides pharmaceutically acceptable salts and compositions of compounds of Formula I that demonstrate protective effects on target cells from HIV infection by binding specifically to the chemokine receptor, thus affecting the binding of a natural ligand to the CCR5 and/or CXCR4 of a target cell.

In another embodiment, the pharmaceutically acceptable salts and compositions of the invention are useful as agents which affect chemokine receptors, such as CCR1, CCR2, CCR3, CCR4, CCR5, CXCR3, CXCR4 where such chemokine receptors have been correlated as being important mediators of many inflammatory as well as immunoregulatory diseases.

Other diseases that are also implicated with chemokines as mediators include angiogenesis, and tumorigenesis such as brain, and breast tumors. Thus, a compound that modulates the activity of such chemokine receptors is useful for the treatment or prevention of such diseases.

The term "modulators" as used herein is intended to encompass antagonist, agonist, partial antagonist, and or partial agonist, i.e., inhibitors, and activators. In one embodiment of the present invention, the pharmaceutically acceptable salts and compositions of compounds of Formula I demonstrate a protective effect against HIV infection by inhibiting the binding of HIV to a chemokine receptor such as CCR5 and/or CXCR4, of a target cell. Such modulation is obtained by a method which comprises contacting a target cell with an amount of the compound which is effective to inhibit the binding of the virus to the chemokine receptor.

The pharmaceutically acceptable salts and compositions of the invention that inhibit chemokine receptor activity and function may be used for the treatment of diseases that are associated with inflammation, including but are not limited to, inflammatory or allergic diseases such as asthma, allergic rhinitis, hypersensitivity lung diseases, hypersensitivity pneumonitis, eosinophilic pneumonias, delayed-type hypersensitivity, interstitial lung disease (ILD) (e.g., idiopathic pulmonary fibrosis, or ILD associated with rheumatoid arthritis, systemic lupus erythematosus, ankylosing spondylitis, systemic sclerosis, Sjogren's syndrome, polymyositis or dermatomyositis); systemic anaphylaxis or hypersensitivity responses, drug allergies, insect sting allergies; autoimmune diseases, such as rheumatoid arthritis, psoriatic arthritis, systemic lupus erythematosus, myastenia gravis, juvenile onset diabetes; glomerulonephritis, autoimmune throiditis, graft rejection, including allograft rejection or graft-versus-host disease; inflammatory bowel diseases, such as Crohn's disease and ulcerative colitis; spondyloarthropathies; scleroderma; psoriasis (including T-cell mediated psoriasis) and inflammatory dermatoses such as dermatitis, eczema, atopic dermatitis, allergic contact dermatitis, urticaria; vasculitis (e.g., necrotizing, cutaneous, and hypersensitivity vasculitis); eosinphilic myotis, eosiniphilic fasciitis; and cancers.

In addition, the pharmaceutically acceptable salts and compositions of the invention that activate or promote chemokine receptor function are used for the treatment of diseases that are associated with immunosuppression such as individuals undergoing chemotherapy, radiation therapy, enhanced wound healing and burn treatment, therapy for autoimmune disease or other drug therapy (e.g., corticosteroid therapy) or combination of conventional drugs used in the treatment of autoimmune diseases and graft/transplantation rejection, which causes immunosuppression; immunosuppression due to congenital deficiency in receptor function or other causes; and infectious diseases, such as parasitic diseases, including but not limited to helminth infections, such as nematodes (round worms); Trichuriasis, Enterobiasis, *Ascariasis*, Hookworm, Strongyloidiasis, Trichinosis, filariasis; trematodes; visceral worms, visceral larva migtrans (e.g., Toxocara), eosinophilic gastroenteritis (e.g., *Anisaki* spp., *Phocanema* ssp.), cutaneous larva migrans (*Ancylostona braziliense, Ancylostoma caninum*); the malaria-causing protozoan *Plasmodium vivax*, Human cytomegalovirus, Herpesvirus saimiri, and Kaposi's sarcoma herpesvirus, also known as human herpesvirus 8, and poxvirus Moluscum contagiosum.

The pharmaceutically acceptable salts and compositions of the invention may be used in combination with any other active agents or pharmaceutical compositions where such combined therapy is useful to modulate chemokine receptor activity and thereby prevent and treat inflammatory and immunoregulatory diseases.

The pharmaceutically acceptable salts and compositions of the invention may further be used in combination with one or more agents useful in the prevention or treatment of HIV. Examples of such agents include:
(1) nucleotide reverse transcriptase inhibitor such as tenofovir disoproxil fumarate; lamivudine/zidovudine; abacavir/lamivudine/zidovudine; emtricitabine; amdoxovir; alovudine; DPC-817; SPD-756; SPD-754;

GS7340; ACH-126,443 (beta)-L-F d4C; didanosine, zalcitabine, stavudine, adefovir, adefovir dipivoxil, fozivudine todoxil, etc.;

(2) non-nucleotide reverse transcriptase inhibitor (including an agent having anti-oxidation activity such as immunocal, oltipraz, etc.) such as nevirapine, delavirdine, efavirenz, loviride, immunocal, oltipraz, TMC-125; DPC-083; capravarine; calanolide A; SJ-3366 series, etc.;

(3) protease inhibitors such as saquinavir, lopinavir/ritonavir, atazanavir, fosamprenavir, tipranavir, TMC-114, DPC-684, indinavir, nelfinavir, amprenavir, palinavir, lasinavir, etc.;

(4) entry inhibitors such as T-20; T-1249; PRO-542; PRO-140; TNX-355; BMS-806 series; and 5-*Helix;*

(5) CCR5-receptor inhibitors such as Sch-C (or SCH351125); Sch-D, and SCH350634; TAK779; UK 427,857 TAK 449; and GSK-873,140 (ONO-4128)

(6) Integrase inhibitors such as L-870,810; GW-810781 (S-1360); and (7) Budding inhibitors such as PA-344; and PA-457.

Combinations of the pharmaceutically acceptable salts and compositions of the invention with HIV agents is not limited to (1), (2), and or (3), but includes combination with any agent useful for the treatment of HIV. Combinations the compounds of the invention and other HIV agents may be administered separately or in conjunction. The administration of one agent may be prior to, concurrent to, or subsequent to the administration of other agent(s).

The pharmaceutically acceptable salts and compositions of the invention may be administered by oral, intramuscular, intraperitoneal, intravenous, intracisternal injection or infusion, subcutaneous injection, transdermal or transmucosal administration or by implant. They may also be administered by inhalation spray, nasal, vaginal, rectal, sublingual, or topical routes and may be formulated, alone or together, in suitable dosage unit formulations containing conventional nontoxic pharmaceutically acceptable carriers, adjuvants and vehicles appropriate for each route of administration.

The pharmaceutically acceptable salts and compositions of the invention are used to treat animals, including mice, rats, horses, cattle, sheep, dogs, cats, and monkeys. The pharmaceutically acceptable salts and compositions of the invention are also effective for use in humans.

The pharmaceutically acceptable salts and compositions of the invention may be administered alone or as an admixture with a pharmaceutically acceptable carrier (e.g., solid formulations such as tablets, capsules, granules, powders, etc.; liquid formulations such as syrups, injections, etc.) may be orally or non-orally administered. Examples of non-oral formulations include injections, drops, suppositories, pessaries.

In the treatment or prevention of conditions which require chemokine receptor modulation an appropriate dosage level will generally be about 0.01 to 500 mg per kg subject body weight per day which can be administered in singe or multiple doses. Preferably, the dosage level will be about 0.1 to about 250 mg/kg per day. It will be understood that the specific dose level and frequency of dosage for any particular patient may be varied and will depend upon a variety of factors including the activity of the specific compound used, the metabolic stability and length of action of that compound, the age, body weight, general health, sex, diet, mode and time of administration, rate of excretion, drug combination, the severity of the particular condition, and the patient undergoing therapy.

Having now generally described the invention, the same will be more readily understood through reference to the following examples which are provided by way of illustration, and are not intended to be limiting of the present invention, unless specified.

EXAMPLES

The following examples are intended to illustrate, but not limit, the invention. For those with skill in the art, it will be apparent that variations and alterations to the reaction conditions to prepare and isolate the described salts may be apparent. Such variations and alterations are intended to be within the scope and spirit of the present invention.

The following abbreviations used in the Examples:
g=grams
mg=milligrams
µL=microliters
mL=milliliters
L=liters
mmol=millimoles
equiv.=stoichiometric equivalents
N=normal
ee=enantiomeric excess
HPLC=High Performance Liquid Chromatography
GC=Gas Chromatography
mp=melting point
DSC=Differential Scanning Calorimetry
NMR=Nuclear Magnetic Resonance Spectrometry
rt=room temperature (ambient)
EtOAc=ethyl acetate
MeOH=methanol
$Et_2O$=diethyl ether
nBuOH=n-Butanol
iPrOH=isopropanol 1. Hydrochloride Salt of the Compound of the Formula I:

It should be noted that all of the hydrochloride salts were synthesized using the same general procedure with varying equivalents of hydrochloric acid.

In a 50 mL round-bottom flask, the compound of the Formula I (0.258 g, 0.738 mmol) was dissolved in reagent grade methanol (5 mL) to generate a colorless solution. The solution was diluted with water (15 mL) and then aqueous hydrochloric acid (0.0978 N, 7.56 mL, 1 equiv.) was added in one portion. The resulting mixture was stirred at 70° C. for one hour. The solvents were removed in vacuo and the resulting clear glass residue was dissolved in water (5 mL) and transferred to a 30 mL plastic bottle. The solution was frozen with liquid nitrogen and then lyophilized over two days to yield a fluffy white solid which was subsequently ground to a fine white powder of the hydrochloride salt of the compound of the Formula I (0.280 g, 98%). HPLC: 98% (>99% ee). GC: $CH_2Cl_2$ (5 ppm), EtOAc (4 ppm), MeOH (0 ppm). Anal. Calcd. for $C_{21}H_{27}N_5 \cdot 1.1$ HCl$\cdot 1.4 H_2O$: C, 60.81; H, 7.51; N, 16.88; Cl, 9.40. Found: C, 60.80; H, 7.20; N, 16.81; Cl, 9.40.

2. Sulfate Salt of the Compound of the Formula I:

In a 50 mL round-bottom flask, the compound of the Formula I (0.513 g, 1.47 mmol) was dissolved in reagent grade methanol (5 mL) to generate a colorless solution. Aqueous sulfuric acid (2 N, 0.735 mL, 1 equiv.) was added in one portion and the reaction mixture was stirred at room temperature for 50 minutes. The solvents were removed in vacuo and the resulting clear glass residue was dissolved in methanol (3 mL) and added dropwise (over 15 minutes) to diethyl ether (150 mL) at room temperature. The resulting white slurry was stirred for 20 minutes and the white solid was isolated via suction filtration (under a steady flow of nitrogen). Nitrogen was forced through the filter cake for 10 minutes and then the solid was broken up with a spatula and transferred to the hot nitrogen apparatus. Hot nitrogen (~75° C.) was blown through a chamber charged with the white solid for 72 hours to yield a fine white powder (0.637 g, 97%). The spectral data for the sulfate salt of the compound of the Formula I is as follows: HPLC: 98% (>99% ee). GC: $Et_2O$ (1839 ppm), $CH_2Cl_2$ (11 ppm), MeOH (0 ppm). Anal. Calcd. for $C_{21}H_{27}N_5.1.1H_2SO_4.1.3H_2O$: C, 52.46; H, 6.67; N, 14.57; S, 7.34. Found: C, 52.60; H, 6.67; N, 14.62; S, 7.19.

The trisulfate salt can be synthesized using the same procedure reported above with the addition of three equivalents of sulphuric acid.

3. Phosphate Salt of the Compound of the Formula I:

In a 50 mL round-bottom flask, the compound of the Formula I (0.393 g, 1.13 mmol) was dissolved in reagent grade methanol (3 mL) to generate a colorless solution. The solution was diluted with water (2 mL) and then aqueous phosphoric acid (14.7 N, 77 µL, 1 equiv.) was added in one portion followed by the addition of water (15 mL). The resulting mixture was stirred at room temperature for 1.5 hours. The solvents were removed in vacuo and the resulting clear glass residue was re-dissolved in water (5 mL) and then the solvents removed again in vacuo (repeat two more times). The final colorless glass residue was ground to a fine powder and dried in vacuo at 40° C. overnight to yield the phosphate salt of the compound of the Formula I (0.441 g, 87%). HPLC: 99% (>99% ee). GC: $CH_2Cl_2$ (3 ppm), MeOH (0 ppm). Anal. Calcd. for $C_{21}H_{27}N_5 \cdot 1.0H_3PO_4 \cdot 0.6H_2O$: C, 55.04; H, 6.86; N, 15.28. Found: C, 55.16; H, 6.66; N, 15.03.

4. Benzoate Salt of the Compound of the Formula I:

To a solution of the compound of the Formula I (1.40 g, 4.01 mmol) in methanol (25 mL) was added benzoic acid (0.488 g, 4.00 mmol). Water (25 mL) was then added to the solution. The resulting solution was concentrated under vacuum via rotary evaporation until slightly cloudy. A small amount of methanol (approximately 0.2 mL) was then added to clarify the solution. The solution was then allowed to slowly evaporate under ambient conditions. Seeding is optional at this point. Crystals formed over a period of 48 hours. The crystals were isolated by filtration. Yield of the benzoate salt of the compound of the Formula I: 0.995 g (51%: $C_{21}H_{27}N_5 \cdot C_7H_6O_2 \cdot H_2O$) as an off-white solid (mp 90° C. (DSC)): $^1$H NMR (300 MHz, $CD_3OD$, δ ppm) 1.35-1.70 (m, 5H), 1.80-2.04 (m, 2H), 2.25 (m, 1H), 2.46 (m, 1H), 2.60-2.90 (m, 5H), 3.95 (d, 1H, J=15.6 Hz), 4.00 (d, 1H, J=15.6 Hz), 4.11 (m, 1H), 7.15-7.21 (m, 3H), 7.35-7.45 (m, 3H), 7.50-7.54 (m, 3H), 7.75-7.95 (m, 2H), 8.49 (d, 1H, J=4.5 Hz); $^{13}$C NMR (75.5 MHz, $CD_3OD$, δ ppm) 22.57, 23.79, 26.65, 26.86, 30.27, 40.59, 51.19, 52.04, 63.49, 115.81, 123.55, 123.77, 128.89, 130.37, 131.50, 137.00, 139.00, 139.36, 139.59, 147.87, 156.26, 157.97, 175.50; Anal. Calcd. $C_{28}H_{33}N_5O_2 \cdot H_2O$: C, 68.69; H, 7.20; N, 14.30; S; Found: C, 68.64; H, 7.18; N, 14.35.

5. Benzenesulfonate Salt of the Compound of the Formula I:

The compound of the Formula I (2.43 g, 6.95 mmol) was dissolved in ethanol (20 mL). Benzene sulfonic acid (1.10 g, 6.95 mmol) was added and the resulting solution was stirred at room temperature for 3 hours. The solvent was then removed under reduced pressure. Ethanol (10 mL) was added to the residue and the solution was cooled to 0° C. Water was added until the solution turned milky. The mixture was warmed to 40° C. until complete dissolution and was cooled slowly to 0° C. with agitation. During the process, the solution was seeded when temperature reached 30° C. with approximately 10 mg of crystalline benzoate salt of the compound of the Formula I. The mixture was stirred and additional hour at 0° C. and the solid was collected by filtration.

The solid was finally dried at 40° C. in vacuo for 1 day to afford the crystalline benzenesulfonate salt of the compound of the Formula I (2.58 g, 74%, $C_{21}H_{27}N_5 \cdot C_6H_6O_3S \cdot 0.5H_2O$) as an off-white solid (mp 87° C. (DSC)): $^1$H NMR (300 MHz, $CD_3OD$, δ ppm) 1.35-1.60 (m, 4H), 1.70 (m, 1H), 1.80-2.10 (m, 2H), 2.25 (m, 1H), 2.46 (m, 1H), 2.60-2.90 (m, 5H), 3.95 (d, 1H, J=15.5 Hz), 4.02 (d, 1H, J=15.5 Hz), 4.14 (m, 1H), 7.15-7.30 (m, 3H), 7.35-7.45 (m, 2H), 7.50-7.60 (m, 3H), 7.75-7.85 (m, 2H), 8.49 (d, 1H, J=4.5 Hz); $^{13}$C NMR (75.5 MHz, $CD_3OD$, δ ppm) 22.84, 24.04, 26.89, 27.03, 30.54, 40.85, 51.41, 52.30, 63.76, 116.00, 123.86, 124.09, 127.31, 129.73, 131.71, 137.32, 139.70, 146.74, 148.13, 156.46, 158.21; Anal. Calcd. $C_{21}H_{27}N_5 \cdot C_6H_6O_3S \cdot 0.5H_2O$: C, 62.77; H, 6.63; N, 13.56; S, 6.21; Found: C, 62.93; H, 6.66; N, 13.61; S, 6.10.

6. 4-Aminobenzoate Salt of the Compound of the Formula I:

To a solution of the compound of the Formula I (2.80 g, 8.01 mmol) in methanol (25 mL) was added a solution of 4-aminobenzoic acid (1.00 g, 8.01 mmol) in methanol (25 mL). Water (50 mL) was then added, and the mixture was then placed under vacuum, and concentrated to the point where the solution turned cloudy. A small amount of methanol was then added to clarify the solution, and the solution was then filtered through a filter paper. The solution was then seeded with a small amount of crystalline 4-aminobenzoate salt, and was cooled to 0° C. for 30 minutes. The mixture was then filtered, and the filter cake was dried under vacuum at room temperature. Yield of off-white crystals of 4-aminobenzoate salt of the compound of the Formula I (mp 139° C. (DSC)): 3.15 g (81%). $^1$H NMR (300 MHz, $CD_3OD$, δ ppm) 1.35-1.65 (m, 5H), 1.80-2.10 (m, 2H), 2.18 (m, 1H), 2.40 (m, 1H), 2.57-2.85 (m, 5H), 3.92 (d, 1H, J=15.5 Hz), 4.02 (d, 1H, J=15.5 Hz), 4.05 (m, 1H), 6.58 (d, 2H, J=8.4 Hz), 7.18 (m, 3H), 7.48-7.54 (m, 3H), 7.72 (d, 2H, J=8.4 Hz), 8.49 (d, 1H, J=3.6 Hz); $^{13}$C NMR (75.5 MHz, $CD_3OD$, δ ppm) 22.56, 23.78, 26.67, 27.03, 30.27, 40.57, 51.21, 52.03, 63.47, 114.80, 115.81, 123.53, 123.74, 127.16, 132.20, 136.98, 139.32, 139.60, 147.86, 152.00, 156.27, 157.97, 176.07; Anal. Calcd. $C_{21}H_{27}N_5 \cdot C_7H_7NO_2 \cdot 0.5H_2O$: C, 67.86; H, 7.12; N, 16.96; Found: C, 68.02; H, 7.04; N, 16.96.

7. 4-Hydroxybenzenesulfonate Salt of the Compound of the Formula I:

To a solution of the compound of the Formula I (1.40 g, 4.01 mmol) in methanol (30 mL) was added a solution of 4-hydroxybenzenesulfonic acid in methanol (40 mL of a 0.10 M solution, 4.0 mmol). The slightly pink solution was filtered through a filter paper, then the mixture was then placed under vacuum, and concentrated to the point where the solution turned cloudy. The solution was then seeded with a small amount of crystalline 4-hydroxybenzenesulfonate salt, and was cooled to 0° C. for 2 hours. The mixture was then filtered, and the filter cake was dried under vacuum at room temperature. Yield of slightly pink crystals of 4-hydroxybenenesulfonate salt of the compound of the Formula I (mp 152° C. (DSC)): 1.11 g (50%). $^1$H NMR (300 MHz, $CD_3OD$, δ ppm) 1.38-1.57 (m, 4H), 1.65 (m, 1H), 1.80-2.10 (m, 2H), 2.21 (m, 1H), 2.43 (m, 1H), 2.62-2.85 (m, 5H), 3.92 (d, 1H, J=15.5 Hz), 4.00 (d, 1H, J=15.5 Hz), 4.12 (m, 1H), 6.75 (d, 2H, J=8.4 Hz), 7.18-7.24 (m, 3H), 7.51-7.55 (m, 3H), 7.64 (d, 2H, J=8.4 Hz), 8.47 (d, 1H, J=4.2 Hz); $^{13}$C NMR (75.5 MHz, $CD_3OD$, δ ppm) 22.56, 23.78, 26.62, 26.76, 30.27, 40.58, 51.12, 52.05, 63.49, 115.85, 123.59, 123.80, 128.87, 137.03, 137.39, 139.40, 147.86, 156.18, 157.93, 160.72; Anal. Calcd. $C_{21}H_{27}N_5 \cdot C_6H_7SO_4 \cdot 1.5H_2O$: C, 58.89; H, 6.59; N, 12.72; S, 5.82; Found: C, 58.84; H, 6.62; N, 12.69; S, 5.76.

8. 4-Aminobenzenesulfonate Salt of the Compound of the Formula I:

To a solution of the compound of the Formula I (2.00 g, 5.72 mmol) in methanol (25 mL) was added 4-aminobenzenesulfonic acid (0.991 g, 5.72 mmol). Water (25 mL) was then added. The mixture was then placed under vacuum, and concentrated to the point where the solution turned cloudy. The solution was opened to the atmosphere, and was allowed to slowly evaporate at room temperature to initiate crystallization. After 24 hours, the mixture was then filtered, and the filter cake was dried under vacuum at room temperature. The mother liquor was collected and was seeded and allowed to evaporate to yield a second crop of crystals. Yield of off-white crystals of 4-aminobenenesulfonate salt of the compound of the Formula I (mp 137-139° C.): 2.21 g (71%, both crops combined). $^1$H NMR (300 MHz, CD$_3$OD, δ ppm) 1.38-1.54 (m, 4H), 1.65 (m, 1H), 1.80-2.10 (m, 2H), 2.18 (m, 1H), 2.46 (m, 1H), 2.62-2.85 (m, 5H), 3.92 (d, 1H, J=15.5 Hz), 4.00 (d, 1H, J=15.5 Hz), 4.12 (m, 1H), 6.61 (d, 2H, J=8.1 Hz), 7.18 (m, 3H), 7.52-7.54 (m, 5H), 8.47 (d, 1H, J=4.2 Hz); $^{13}$C NMR (75.5 MHz, CD$_3$OD, 6 ppm) 22.57, 23.78, 26.62, 26.78, 30.26, 40.58, 51.12, 52.05, 63.47, 114.76, 115.93, 123.57, 123.79, 128.43, 134.59, 137.03, 139.37, 147.87, 151.68, 156.21, 157.94; Anal. Calcd. C$_{21}$H$_{27}$N$_5$'C$_6$H$_7$NSO$_3$.H$_2$O: C, 59.98; H, 6.71; N, 15.54; S, 5.93; Found: C, 60.06; H, 6.65; N, 15.59; S, 5.79.

9a. 4-Hydroxybenzoate Salt of the Compound of the Formula I (Procedure A):

To a solution of the compound of the Formula I (6.99 g, 20.0 mmol) in methanol (50 mL) was added 4-hydroxybenzoic acid (2.76 g, 20.0 mmol). Water (30 mL) was then added. The mixture was then placed under vacuum, and concentrated to the point where the solution turned cloudy. A small amount of methanol (about 1 mL) was added to re-clarify the solution, which was then filtered through a filter paper. The solution was then seeded with a small amount of crystalline 4-hydroxybenzoate salt, and was then cooled to 0° C. for 30 minutes, during which time, white crystals formed. The mixture was then filtered. The mother liquor was then re-filtered to give two crops of crystals of the 4-hydroxybenzoate salt of the compound of the Formula I (mp 151° C. (DSC)): 8.86 g (91%, both crops combined). $^1$H NMR (300 MHz, CD$_3$OD, δ ppm) 1.38-1.54 (m, 4H), 1.65 (m, 1H), 1.84-2.05 (m, 2H), 2.18 (m, 1H), 2.46 (m, 1H), 2.62-2.85 (m, 5H), 3.93 (d, 1H, J=15.6 Hz), 4.03 (d, 1H, J=15.5 Hz), 4.12 (dd, 1H, J=10.8, 3.0 Hz), 6.70 (d, 2H, J=8.7 Hz), 7.17-7.22 (m, 3H), 7.52-7.54 (m, 3H), 7.80 (d, 2H, J=8.4 Hz), 8.47 (d, 1H, J=4.2 Hz); $^{13}$C NMR (75.5 MHz, CD$_3$OD, δ ppm) 22.56, 23.74, 26.65, 26.94, 30.28, 40.57, 51.22, 52.04, 63.51, 115.48, 115.81, 123.56, 123.79, 129.83, 132.43, 137.03, 139.38, 147.86, 156.26, 157.95, 161.15, 175.60; Anal. Calcd. C$_{21}$H$_{27}$N$_5$.C$_7$H$_6$O$_3$.0.4H$_2$O: C, 67.97; H, 6.88; N, 14.15; Found: C, 68.02; H, 6.93; N, 14.24.

9b. 4-Hydroxybenzoate Salt of the Compound of the Formula I (Procedure B):

The compound of the Formula I (37.2 g, 130 mmol) was dissolved in MeOH (260 mL) at room temperature. 4-Hydroxybenzoic acid (17.94 g, 0.9 eq. based on theoretical yield) was added and the ratio was checked by NMR. Additional 4-hydroxybenzoic acid was added to ensure 5~10% excess of the acid. The pH of the mixture was checked by moistened pH paper, and more acid or NaOH was added if necessary to bring the pH to 7~8. The mixture was heated to 50° C. and water (720 mL) was added. The mixture was slowly cooled and was seeded at ~40° C. Crystals began to form. After stirring at room temperature overnight, the mixture was filtered and the filter cake was washed with ice-cold aqueous MeOH (3:1 water-MeOH, 500 mL in two washings). The solid was dried under a stream of N$_2$ and further dried under high vacuum overnight to give the final product as slightly off-white powder: 43.3 g (71%). Purity: 99.9% by HPLC; chiral Purity (HPLC): 97.1% e.e. mp 151° C. (DSC). The spectral data is consistent with that listed in procedure 9a.

9c. 4-Hydroxybenzoate Salt of the Compound of the Formula I (Procedure C):

A solution of the compound of the Formula I (560 g, 1.6 mol) in water at pH 9-10 (2.3 L) was extracted with two portions of n-butanol (2.3 L each). The combined n-butanol fractions containing the compound of the Formula I were then concentrated under reduced pressure at a temperature of approximately 35° C. to a volume of approximately 1.5 L. Isopropanol (3.5 L) was then added and the solution was concentrated to a final volume of 1.5 L under reduced pressure at approximately 35° C. Analysis for water content was then conducted (pass of 0.1% or less: if water content is above 0.1% w/w, another fraction of isopropanol is added and the distillation is repeated). A further 3.5 L of isopropanol was added to the solution.

In a separate vessel, 4-hydroxybenzoic acid (110 g, 0.8 mol, 0.5 eq.) was dissolved in isopropanol (3.5 L), and the acid solution was added to the isopropanol solution of the compound of the Formula I. The relative ratios of 4-hydroxybenzoic acid to the compound of the Formula I were checked by $^1$H NMR, and further portions (0.1 eq.) are added until a target of 100-110 mol % 4-hydroxybenzoic acid to compound of the Formula I was reached. The solution was then concentrated under reduced pressure at 30-50° C. to a final volume of approximately 1.5 L, and the solvent ratio of n-Butanol to isopropanol was checked by $^1$H NMR (expecting approximately 25% n-Butanol relative to isopropanol). The solution was then filtered, and isopropanol (0.75 L) is then added. The solution was warmed to 50-55° C., and water (9 L) was then added slowly, maintaining the temperature between 50-55° C. The pH of the solution was then adjusted to 7.5-8 with 10% w/w sodium hydroxide. The solution was cooled to 38-40° C., and seed crystals (3.8 g) were then added to initiate crystallization. After stirring at 38-40° C. for approximately 45 minutes, the mixture was cooled over 2-3 hours to 0-5° C. The slurry was then stirred at 0-5° C. for 1 hour. The product 4-hydroxybenzoic acid salt of the compound of the Formula I was isolated by filtration, and the filter cake was dried at 40-50° C. in a vacuum oven until the water content was <2.0% w/w. 620 g (77%) of the 4-hydroxybenzoic acid salt of the compound of the Formula I was isolated as a fluffy off-white crystalline solid: Purity 96.8% (w/w assay on an anhydrous basis by HPLC: Total impurities 0.14% w/w); Chiral Purity >99% e.e. The Spectral data is consistent with that listed in Procedure 9a.

10. Orotate Salt of the Compound of the Formula I:

In a 50 mL round-bottom flask, the compound of the Formula I (2.00 g, 5.73 mmol) was dissolved in reagent grade methanol (20 mL) to generate a colorless solution. The solution was diluted with water (5 mL) and then orotic acid monohydrate (1.00 g, 5.73 mmol) was added and the resulting mixture was stirred at room temperature for one hour. The solvents were removed in vacuo and the resulting pale yellow glass residue was suspended in ethyl acetate (30 mL). The pale yellow slurry was heated to 80° C. and methanol was added slowly until the solid completely dissolved (18 mL MeOH in total). Five drops of water was then added to aid in crystallization and the pale yellow solution was cooled slowly to room temperature resulting in the formation of a white crystalline solid. After 18 hours at room temperature the solid was broken up with a spatula and the white microcrystalline solid was isolated via suction filtration and then dried in vacuo at 50° C. for 16 hours (2.75 g, 95%). HPLC: 99.7% (>99% ee). GC: EtOAc (45 ppm), MeOH (11 ppm).

11. N$^1$-(1H-Benzimidazol-2-ylmethyl)-N$^1$-(5,6,7,8-tetrahydro-quinolin-8-yl)-butane-1,4-diamine Free Base and Crystalline Salts (Specified in Table 1) Stability Samples Preparation and Storage Conditions:

About 100 mg of material was placed in a clear 4 ml vial. Lids were placed tightly on the vials by hand and the vials were stored at 25° C./60% RH, 40° C./75% RH and 70° C. in desiccator. At each time point, about 0.3 to 0.6 mg sample was taken out and dissolved in 1:10.1 M HCl:MeOH to make a 0.5 mg/mL solution. The samples were analyzed by HPLC and the peak area percentages of the compound N$^1$-(1H-Benzimidazol-2-ylmethyl)-N$^1$-(5,6,7,8-tetrahydro-quinolin-8-yl)-butane-1,4-diamine and degradation product were used as stability indication.

Table 1 illustrates the stability profile, at various temperatures, of salt types of N$^1$-(1H-Benzimidazol-2-ylmethyl)-N$^1$-(5,6,7,8-tetrahydro-quinolin-8-yl)-butane-1,4-diamine.

TABLE 1

| Salt | Months | 70° C. | 40° C./75% RH | 25° C./60% RH |
|---|---|---|---|---|
| Free base | 1 | 45.9% | 86.6% | 99.5% |
| p-hydroxybenzoate | 3 | 99.3% | 99.8% | 99.7% |
| p-aminobenzoate | 3 | 99.0% | 99.5% | 99.7% |
| p-hydroxybenzene sulfonate | 1 | 99.8% | 99.9% | 100.0% |
| p-aminobenzene sulfonate | 1 | 99.2% | 99.7% | 100.0% |
| Benzene sulfonate | 0.5 | 88.4% | 99.2% | 99.9% |
| Benzoate | 1 | 85.1% | 99.5% | 100.0% |
| Orotate | 0.5 | 95.0% | 99.8% | 100.0% |

It is understood that the foregoing detailed description and accompanying examples are merely illustrative, and are not to be taken as limitations upon the scope of the invention. Various changes and modifications to the disclosed embodiments will be apparent to those skilled in the art. Such changes and modifications, including without limitation those relating to intermediates, syntheses, formulations and/or methods of use of the invention, may be made without departing from the spirit and scope thereof. U.S. patents and publications referenced herein are incorporated by reference.

The invention claimed is:

1. A crystalline pharmaceutically acceptable salt of a compound of Formula I

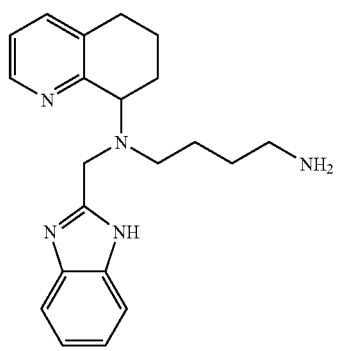

I wherein said salt is benzoate, 4-aminobenzoate, 4-hydroxybenzoate, orotate, 4-hydroxybenzenesulfonate, or 4-aminobenzenesulfonate.

2. The salt of claim 1, wherein said salt is 4-aminobenzoate, 4-hydroxybenzenesulfonate, 4-aminobenzenesulfonate, or orotate.

3. The salt of claim 1, wherein said salt is 4-hydroxybenzoate.

4. A pharmaceutical composition comprising a crystalline pharmaceutically acceptable salt of a compound of Formula I

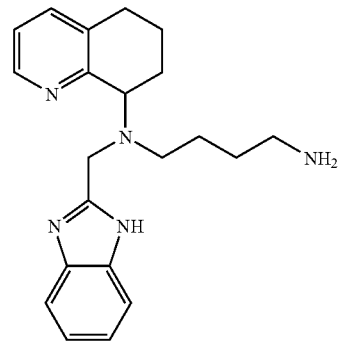

I wherein said salt is benzoate, 4-aminobenzoate, 4-hydroxybenzoate, orotate, 4-hydroxybenzenesulfonate, or 4-aminobenzenesulfonate, and a pharmaceutically acceptable diluent.

5. The composition of claim 4, wherein said salt is 4-aminobenzoate, 4-hydroxybenzenesulfonate, 4-aminobenzenesulfonate, or orotate.

6. The composition of claim 4, wherein said salt is 4-hydroxybenzoate.

7. A crystalline benzoate salt of a compound of Formula I

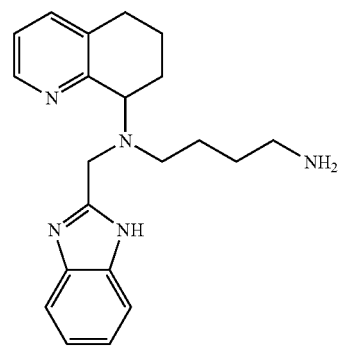

I having less hydroscopicity than the hydrobromide or hydrochloric salt of said compound of Formula I.

8. The salt of claim 7, wherein said benzoate is 4-hydroxybenzoate.

9. The salt of claim 7, wherein said salt is more stable in storage than the hydrobromide or hydrochloride salt of said compound of Formula I.

10. The salt of claim 7, wherein said salt has an improved stability as compared to the free base at about 30 degrees Celsius and above; at about 40 degrees Celsius and above; or at about 70 degrees Celsius and above.

* * * * *